(12) United States Patent
Baykut et al.

(10) Patent No.: US 8,188,424 B2
(45) Date of Patent: May 29, 2012

(54) PREPARATIVE ION MOBILITY SPECTROMETRY

(75) Inventors: Gökhan Baykut, Bremen (DE); Jonas Bergquist, Uppasala (SE)

(73) Assignee: Bruker Daltonik GmbH, Bremen (DE)

( * ) Notice: Subject to any disclaimer, the term of this patent is extended or adjusted under 35 U.S.C. 154(b) by 1082 days.

(21) Appl. No.: 11/506,162

(22) Filed: Aug. 17, 2006

(65) Prior Publication Data

US 2008/0042055 A1 Feb. 21, 2008

(51) Int. Cl.
*H01J 49/00* (2006.01)
(52) U.S. Cl. ............ 250/287; 250/281; 250/282
(58) Field of Classification Search ........ 250/281–300
See application file for complete search history.

(56) References Cited

U.S. PATENT DOCUMENTS

| | | | |
|---|---|---|---|
| 5,905,258 A | 5/1999 | Clemmer et al. | |
| 6,878,930 B1 * | 4/2005 | Willoughby et al. | 250/281 |
| 6,960,761 B2 | 11/2005 | Clemmer | |
| 7,170,052 B2 * | 1/2007 | Furutani et al. | 250/287 |
| 7,429,729 B2 * | 9/2008 | Schultz et al. | 250/287 |
| 7,482,582 B2 * | 1/2009 | Raznikov et al. | 250/287 |
| 2003/0226963 A1 * | 12/2003 | Cooks et al. | 250/283 |
| 2005/0023453 A1 * | 2/2005 | Bateman et al. | 250/288 |
| 2005/0189485 A1 * | 9/2005 | McLean et al. | 250/287 |
| 2005/0194544 A1 * | 9/2005 | Vestal et al. | 250/425 |
| 2005/0230615 A1 * | 10/2005 | Furutani et al. | 250/287 |
| 2005/0258364 A1 * | 11/2005 | Whitehouse et al. | 250/292 |
| 2006/0289746 A1 * | 12/2006 | Raznikov et al. | 250/294 |
| 2006/0289747 A1 * | 12/2006 | Schultz et al. | 250/294 |

* cited by examiner

*Primary Examiner* — Phillip A Johnston
*Assistant Examiner* — Andrew Smyth
(74) *Attorney, Agent, or Firm* — Law Offices of Paul E. Kudirka

(57) ABSTRACT

In an ion mobility spectrometer, ions are generated, mobility-separated and deposited on a receiver, preferably at spatially separated positions by soft landing or crash landing techniques. The ion mobility spectrometer can be a stand-alone instrument or part of a hybrid analysis instrument. To analyze the deposited ions, the receiver is removed from the vacuum system of the ion mobility spectrometer and introduced into an analytical instrument. Various physical, chemical, and biological analysis techniques and instrumentation can be used, such as mass spectrometry or surface analytical techniques, by selecting a special receiver suitable for the desired analytical technique.

15 Claims, 9 Drawing Sheets

PREPARATIVE ION MOBILITY SPECTROMETRY

FIELD OF THE INVENTION

Apparatus and method of this invention relates to ion mobility spectrometry.

BACKGROUND OF THE INVENTION

The introduction of electrospray ionization (ESI) and matrix-assisted laser desorption ionization (MALDI) techniques helped mass spectrometry to experience a giant leap in the analytical chemistry of large molecules and biopolymers during the last two decades. Mass spectrometers with higher-accuracy mass detection capability (such as Fourier transform ion cyclotron resonance mass spectrometers, FT-ICR MS, or electrospray orthogonal time-of-flight mass spectrometers ESI-TOF MS) satisfied some needs for the accurate mass information. Additionally, different MS/MS capabilities allowed to obtain important structural information upon fragmentation of selected ions especially by collisions with neutral particles (collision induced dissociation, CID), by sequential absorption of multiple infrared photons from a $CO_2$ laser (infrared multiphoton dissociation, IRMPD), by capturing low energy electrons (electron capture dissociation, ECD) or by electron transfer from a negative ion (electron transfer dissociation, ETD).

In biochemistry, particularly for characterization of proteins, the amino acid sequence is important analytical information. However, the physiologic activity of a protein does not only depend on its amino acid sequence. Protein chains fold to form secondary structures (alpha helices, beta sheets), which in turn fold further and build tertiary structures in order to take more stable conformations. Additionally, in some cases, a number of folded protein units form non-covalent agglomerates (quaternary structures): Hemoglobin for example forms its characteristic tetrameric structure with two alpha and two beta chains.

Recent experience with proteins teaches that neurodegenerative disorders like Alzheimer's, Parkinson's, Huntington's diseases, Amyotrophic lateral sclerosis (ALS), and transmissible spongiform encephalopathies (TSE) like bovine spongiform encephalopathy (BSE) or the human equivalent Creutzfeld-Jakob disease (CJD) are closely related to misfolding of proteins. Thus, studies to obtain information about tertiary protein structures became crucial. For discovering physiologic activities of proteins, the information about their folding geometry is complementary to their basic amino acid sequence information.

Overall geometric changes of proteins are also observed due to other effects: Many proteins are post translationally modified. About 70% of the active proteins in human organism are glycosylated. Posttranslational modifications (PTMs) also induce differences in protein geometry. Modified proteins containing a number of polar groups like phosphates or sugar groups, both steric and electronic interactions within the molecule increase its potential energy. The molecule undergoes conformational changes to accommodate the new groups without losing much of its stability. Therefore, phosphorylated and glycosylated proteins can have different overall geometry than their unmodified analogues. PTMs obviously alter the mass of the protein, and thus, the overall mass of a modified protein will be different. Proteins that have just some small differences, e.g. some post translational modifications, are isoforms. Isoforms can also have very different geometric cross sections. Structural characterization of various isoforms of large proteins, in terms of determining positions, number, and kind of particular modifications can be difficult using the mostly applied fragmentation (MS/MS) methods (CID, IRMPD), since during these processes the PTM groups are not protected. Only ECD and ETD methods can protect the PTMs, but both of them are limited to certain types of mass spectrometers.

Structural or conformational isomers have different geometric appearance but exactly the same mass. Thus, they cannot be recognized as different species in regular mass spectrometry. One of the most efficient ways to recognize and separate structural or conformational isomers is the ion mobility separation. Ions are accelerated in an ion mobility cell. An ion mobility cell has an inert collision gas (for example helium). Ions are accelerated in an electric field. Due to the collisions with gas molecules the ions are also exposed to a drag force and therefore move through the cell with a constant velocity proportional to the electric field. The proportionality constant is called "ion mobility" and is a function of the temperature, pressure, ion charge, ion collision cross section, and the reduced mass. Ions with the same mass but with different collisions cross sections have different mobilities. If different conformational isomers of the same compound are accelerated in an ion mobility cell, the isomer with the smallest geometric cross section will have the highest ion mobility. Protonated molecules of a tightly folded protein conformer have smaller geometric cross section and therefore will be exposed during their flight through the mobility cell a smaller number of collisions. Ions with open (unfolded) conformation will be exposed to a larger number of collisions and therefore fly slower than the tightly folded isomer with the same mass to charge ratio. Unfolded isomers exit the mobility cell at a later "arrival time" (as illustrated in FIGS. 1a and 1b, described below).

The information to be extracted from ion mobility separation measurements is in various levels. Ions of exactly the same mass-to-charge ratio but with different conformation will be separated. From absolute values of the ion mobility cross sections in a certain collision gas (e.g. helium) various ion conformation possibilities can be calculated using available force field programs e.g. AMBER (Assisted Model Building and Energy Refinement) or CHARMM (Chemistry at HARvard Macromolecular Mechanics). Measurement of relative geometric cross sections is also very often applied in the ion mobility separated mass spectrometry for studying changes and for discovering the existence of different isomeric structures.

In the past, the main application of ion mobility spectrometers was the detection of chemical warfare agents, drugs, and explosives. Ion mobility spectrometers specifically built for on site detections of these compound classes are usually small hand-held detectors. The mobility-separation process of ions in these devices is performed in a collision gas. Unlike for mass spectrometers, no vacuum is required in these ion mobility spectrometers. Thus, no expensive pumping systems are needed in these devices, and the production of them is relatively inexpensive.

In the recent years, as the importance of the ion mobility separation has increased for chemical and biological research, ion mobility separation cells were integrated to mass spectrometric systems to combine the ionic cross section information of isomeric compounds with their mass information. One major drawback of these hybrid instruments is the high pressure range of the ion mobility separation part, which is not really compatible with the rest of the mass spectrometric equipment. For decent ion mobility separations, pressures of 1 mbar or higher are required, where mostly helium is used as a collision gas (sometimes argon is also used). High pressure cells in mass spectrometric vacuum systems have always been a challenge for pumping. Large pumping units are crucial to pump out the collision gas in the high pressure chamber. Additionally, high pressure chambers have to be isolated from the rest of the mass spectrometer by carefully designed pumping stages. These measures increase the required space to accommodate the ion mobility separators, complicate the construction these hybrid systems and the cost of the final equipment. Solutions always involve compromises on both sides.

Further problems arise from coupling the ion mobility separation cell to a succeeding analyzer (e.g. mass analyzers) concerning the timing of the mobility-separated ions leaving the ion mobility separation cell and entering the analyzer (e.g. mass analyzer). The succeeding analyzer must generally be much faster than the ion mobility separation which is even not easily achievable for fast scanning mass analyzers like time-of-flight mass spectrometers with orthogonal ion injection (OTOF-MS). If the mobility cell has conventional dimensions, the time separation of, for instance, the conformational isomers of proteins are in the range of hundreds of microseconds.

As mentioned, this separation time becomes, even for the time-of-flight mass spectrometers, a challenging problem. Other mass spectrometers are much slower. In the case of Fourier transform ion cyclotron resonance mass spectrometry (FT-ICR MS), the time from the ionization process to the detection time can be several hundred milliseconds to several seconds. There is practically no way to fully use ion mobility separation spectrum. The only way to use an ion mobility-FT-ICR MS hybrid instrument is to apply a so-called slicing method. In this method ions of a predefined ion mobility window can be trapped and collected in a linear RF multipole ion trap and then are transferred into the ion cyclotron resonance cell for analysis. An on-line analysis of a complete ion mobility spectrum is not possible here due to time reasons.

In regular ion mobility spectrometers, the ion mobility separation cell has an ion detection device at the exit. In recent years ion mobility separation has been combined with mass spectrometry so that the mobility separated isomers can be mass analyzed by mass spectrometry. U.S. Pat. No. 5,905,258 (David E. Clemmer and James P. Reilly) and U.S. Pat. No. 6,960,761 (David E. Clemmer) describe mass spectrometric systems equipped with ion mobility separation devices.

SUMMARY OF THE INVENTION

The present invention comprises an apparatus and a method for generating ions, separating these ions according to their ion mobility, and depositing the mobility-separated ions onto a target object that in the following discussion will be called a "receiver". The mobility-separated ions can be spatially focused prior to the deposition on the receiver. The deposition can be a "soft landing" without fragmentation or a "crash landing" with fragmentation.

Mobility-separated ions of different ion mobilities are preferably deposited on spatially separated positions on the receiver. This is facilitated by moving the receiver or by using ion deflection optics to transfer mobility-separated ions of different mobility to spatially different positions on the receiver. As a basic advantage, the present invention offers the novel option of analyzing the mobility separated ions by splitting the processes of ion mobility separation and the analysis into two basically different devices. To analyze the deposited ions, the receiver is removed and introduced to an analytical instrument. Various physical, chemical, and biological analysis techniques and instrumentation can be used, such as mass spectrometry or surface analytical techniques, by selecting a special receiver suitable for the desired analytical technique. Once the separated compounds are deposited on the receiver, they can be kept under predefined conditions to be used later in an adequate analysis instrument, which can in principle be much slower than the ion mobility spectrometer: The time for the analysis can be much longer than the mobility separation process of the ions.

It is known that, depending on the physical and chemical properties of the deposition surface and on the chemical constitution of the ions, they may be deposited as ions, or they may get neutralized during or after the deposition process and remain as neutral species at the surface. In the following, the expression "ion deposition" will be used regardless if ionic character of the deposited species is conserved in the deposited phase or not. Similarly, the deposited species, which were ions in the gas phase prior to deposition, will be called in the following "deposited ions". After the deposition, they may still be ionic species, or may have lost their ionic character.

In order to deposit intact ions, their kinetic energy has to be kept very low and carefully controlled during their approach to the receiver. On the other hand, as known from mass spectrometric techniques, a controlled fragmentation of ions is a valuable source of structural information. Thus, in addition to depositing intact ions of a certain ion mobility window by a "soft landing", the ability to deposit ions by a "crash landing" on spatially different but assigned positions is important. In this case, the energy of the ions is increased, if necessary gradually, and ions are deposited by a harder landing. This will be called in the following description a "crash landing". This process deposits fragments of ions, which already have the structural information. In other words, this is a way of depositing the fragmentation information. If the receiver is later studied by a mass spectrometric analysis system, the already deposited fragmentation information may be satisfactory. An additional fragmentation in the mass spectrometer may not be necessary for structural studies.

The ion mobility spectrometer in the present invention offers the option of repeatedly pulsing ions into the ion mobility separation cell and repeatedly depositing the mobility-separated ions onto the receiver surface at spatially separated positions. The cycle of pulses, separations, and depositions can be synchronized with the motion (e.g. rotation) of the receiver or with the motion of the ion beam, so that ions from the same ion mobility time window are deposited always at the same position. In this way, an accumulative deposition is possible.

The ions can also be selected or separated with regard to their mass to charge ratio prior to the separation in the ion mobility separation cell by using a mass analyzer, like a quadrupole mass filter or a 2D or 3D quadrupole ion trap.

A "soft landing" of separated ions requires a deceleration of ions to very low energies and a careful control of the kinetic energy during this landing process. On the other hand, the separated ions have to be focused to land on spatially separated positions. Therefore, an ion optical unit, which contains an Einzel lens or a more sophisticated lens stack, can be used for controlling the kinetic energy of separated ions and for focusing those to individual positions on the receiver. As mentioned above, the ion optical unit for deposition also contains ion deflection optics.

The temperature of the receiver is an important parameter for some of the physical and chemical properties of the receiver or for the coating at the receiver surface, especially the viscosity and vapor pressure of a fluidic layer. It has to be cooled down, if necessary, or heated. Therefore, in some embodiments, it is important that the receiver is temperature-controlled.

The ion mobility separation cell to be used in this invention can be a linear ion mobility separation cell; it can also be a mobility separation device of other technologies to achieve a separated deflection of the ions. The latter arrive not only temporally separated, but they directly travel to spatially separated detectors. Variations of separating field asymmetric waveform ion mobility (FAIMS) cells can also be used.

BRIEF DESCRIPTION OF THE DRAWINGS

The above and further advantages of the invention may be better understood by referring to the following description in conjunction with the accompanying drawings in which:

FIG. 1a is a diagram showing that the proteins enter the ion mobility cell at the same time.

FIG. 1b is a block schematic diagram of the construction of a conventional ion mobility separation cell. Protein ions with the open folding state are exposed to a larger number of collisions and spend more time in ion mobility cell than the isomers with the compact folding state. Thus, compact ions exit the cell first and the larger ions follow later.

FIG. 1c is a diagram showing the exit sequence of ions out of the cell. Although folded protein ions, as well as the unfolded ones also tend to rotate during their travel through the mobility cell, the average geometric cross section of unfolded ions will still be larger, thereby causing a longer delay and a longer retention time.

DETAILED DESCRIPTION

Figure 1:
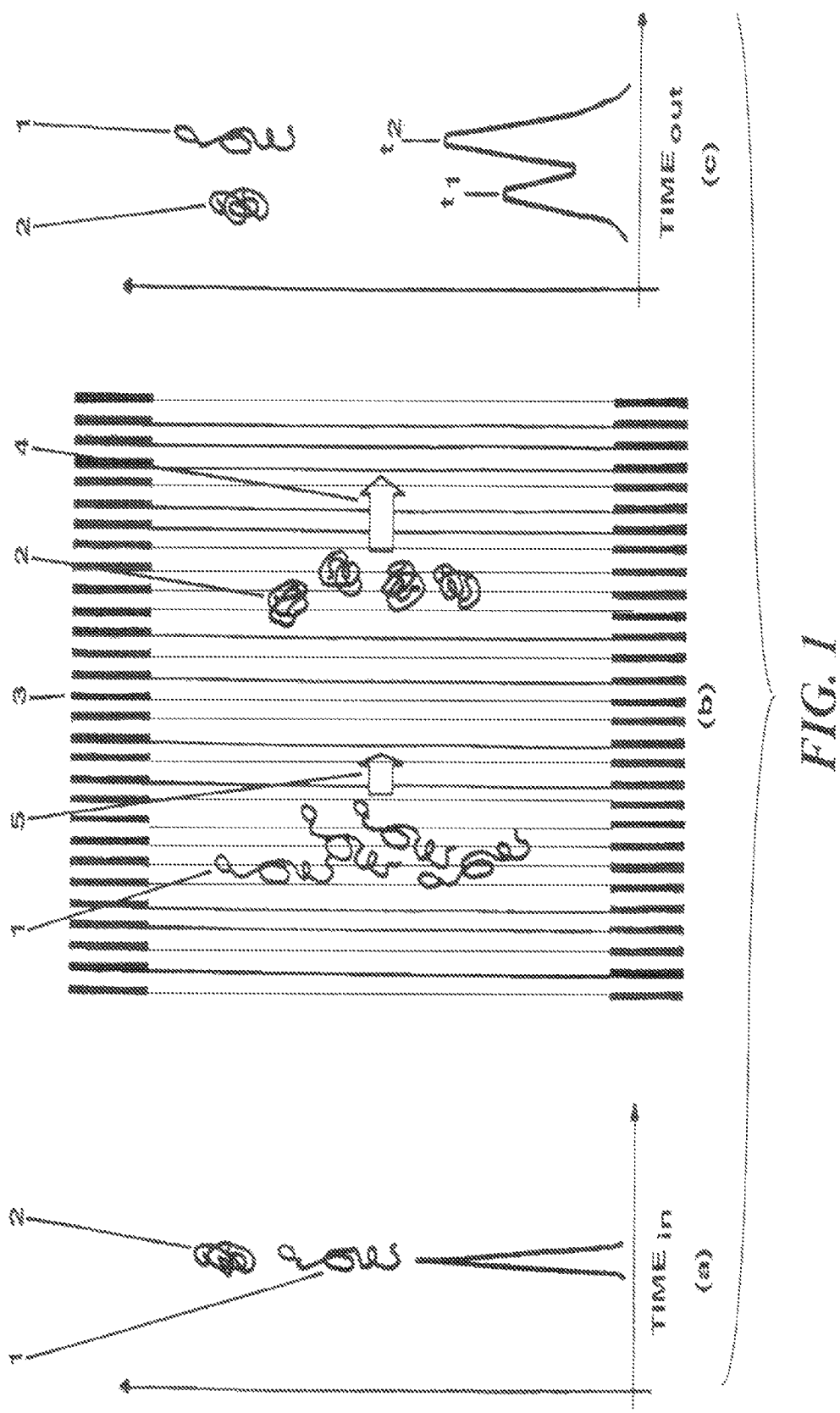
FIGS. 1a-1c schematically illustrate the conventional principle of the ion mobility separation using proteins as an example. Protein ions of same mass-to-charge ratio but different folding states are entering the ion mobility separation cell.

The present invention separates the tasks of ion mobility separation and the mass spectrometric detection. These two tasks are performed in two separate instruments in order to solve the vacuum system-related problems of mass spectrometry. Dividing ion mobility separation and analysis into two separate instruments also eliminates all problems related to time limitations in detection. Additionally, in the present invention ions are generated and mobility-separated in a cell under ideal conditions of ion mobility spectrometry. At the end of this operation, separated ions are deposited by soft landing on a receiver, which is a sample holder for the analysis of the deposited ions. As the ion mobility spectrometer is separated from the analysis system, both the ion mobility spectrometer and the analysis system can operate under their own ideal conditions. Upon completion of the deposition event, the receiver, which is a sample holder, is transferred to the analysis device.

Once the mobility separated ions are deposited, the analysis of them can be performed by any physical, chemical and biological analysis method, in entirely different conditions than the ion mobility separation requires. The analyzer device for investigating the deposited ions can be a mass spectrometer with a laser desorption (with or without matrix) ionization source or with an electrospray ion source. It can also be a surface plasmon resonance device, or a photoelectron spectrometer, or an atomic force microscope, or a scanning tunneling microscope, or a field ion microscope, or an X-ray absorption fine structure analysis device. The present invention offers the opportunity of depositing the mobility-separated ions on any receiver that is a specific sample holder suitable for the selected analytical method to be applied afterwards. Thus, the receiver can be a sample holder for surface analytical techniques comprising photoelectron spectroscopy, or atomic force microscopy, or surface plasmon resonance, or SIMS, or Auger electron spectroscopy, or ballistic electron microscopy, or scanning tunneling microscopy, or extended X-ray absorption fine structure analysis, or field ion microscopy, or field emission microscopy, or Fourier transform infrared reflectance spectroscopy.

The receiver for the ion deposition can be made of various materials (i.e. metal, ceramic, glass, polymer) of various shapes (i.e. as a plain rectangular platform, or a disk, or a cylindrical drum) and the receiver surface can have various structures (e.g. plain and/or welled, blank or porous). Further, the receiver surface can be a physically, chemically, biochemically, or biologically prepared surface (e.g. treated to obtain a suitable dielectric constant, or hydrophobicity, or acidity, or basicity, or a surface with a fluidic layer, or a surface covered with selected bacteria, or cells, or enzymes, or immobilized proteins, antibodies) for accepting the soft landing ions and for keeping them intact. If the surface of the receiver is covered with a fluidic layer, the properties of this layer, e.g. its chemical composition, acidity, basicity, hydrophobicity, dielectric constant, viscosity and vapor pressure should be optimized for the deposition of the ions of interest. For depositing some proteins, fluidic surfaces based on mixtures of glycerol and various sugar solutions can be prepared. Adequate physical, chemical, or biochemical treatment of the receiver surface will be required to obtain a suitable surface for chemical and biochemical analysis methods, e.g. immunohistochemical analysis, affinity based detection techniques, using aptamers, affibodies, antibodies.

Ions being deposited can be kept on the surface by physical attachment or by chemical bonding onto the surface material. The latter can be a weak non-covalent interaction between the surface and the deposited ions, or it can be an ionic or a covalent chemical bond. During deposition of ions onto a porous surface on the receiver, the surface-deposited ions can penetrate the pores and cover the surface in the pores, so that it virtually becomes a volume process. If deposited ions undergo a chemical reaction with the surface that continues in the solid phase, the deposition may become in this case a real volume process.

For reaching every position on the surface of the receiver during the deposition, either the ion beam can be moved using adequate deflector ion optics, or the receiver can be moved. If the deposition ion beam is fixed, every point of the receiver surface can be reached by combining linear and rotational motions of the receiver. If the deposition beam is moved, more complex motions can be programmed for reaching every position on the receiver. To increase the speed of the distribution both the deposition beam and the receiver can be moved using adequate software tools.

Using a rotating plate or a rotating cylindrical drum as receiver has many advantages particularly when depositing mobility-separated ions with short time differences between each other. A rotating receiver can be synchronized with the deposition pulse of a separated ion type, so that the same isomers can be deposited an exactly the same position. The separation in regular ion mobility separation cells may be in the order of some hundreds of microseconds. The x-y-motion actuation for a planar plate is normally too slow to switch between receiver positions for spatially separating the ions deposited. Rotation speed is an additional factor determining the resolution of the deposition.

In another embodiment for depositing mobility-separated ions on a receiver, an ion deflector unit can be used. The simplest example of an ion deflector is a pair of plates to which a potential difference is applied. In order to control the direction of an ion beam in two dimensions (x and y) there will be two pairs of plates necessary in one pair in x and one pair in y direction. More complex multi electrode beam deflector units can also be used. A computer-controlled movement of both the ion beam and the receiver increases the speed of spatially separated deposition.

In longer ion drift distances in a mobility cell, ions tend to diffuse away from the axis by radial diffusion and get defocused. To overcome this effect, the ion mobility separation can be in an RF multipole electric field to guide the ions and prevent their radial diffusion during their axial flight through the cell. U.S. Pat. No. 6,630,662 (Alexandre V. Loboda) describes an RF quadrupole ion guide with sliced electrodes to apply axial electric field used as an ion mobility separation cell. This construction allows the building of extremely long ion mobility cells if required, and longer ion mobility cells in turn lead to better resolution in ion separation. Thus, in this case, the spot switching motion of either the receiver or the ion beam during the deposition of the mobility separated ions does not need to be too fast.

Ion kinetic energies considered for soft landing and crash landing can depend on the chemical constitution of the ions to be deposited. This can be discussed in terms of bond energies. Organic ions of biological origin have large number of carbon-carbon bonds (single and double bonds), carbon-nitrogen, carbon-oxygen bonds, and phosphorus-oxygen bonds. Kinetic energies of ions during landing basically determine the destiny of the ion when landed. Carbon-carbon single bond energy is about 348 kJ/mol, (3.61 eV); double and triple bond energies are much higher. Carbon-nitrogen single bond energy is 292 kJ/mol, (3.04 eV), and carbon-oxygen single bond energy is about 351 kJ/mol (3.66 eV). According to these numbers, an ion landing with kinetic energies over 3 eV is already critical for organic molecules and can cause a crash landing. Therefore kinetic energies below 3 eV will definitely assure a soft landing. Although at energies above 3 eV an ion could end up with crash landing on the receiver, if this is a large ion, like a protonated insulin ion (m/z≅5800), a slightly higher energy then 3 eV may not result in fragmentation. Such a complex ion has large number of degrees of freedom and the acquired internal energy spreads out in the molecule in form of vibrational energies. The excited ion can undergo unimolecular fragmentation at a rate depending on the numbers and frequencies of its vibrational modes. For similar cases in gas phase, when ions are excited by collisions with molecules, prediction of unimolecular fragmentation rate constants requires theories considering vibrational and also rotational states, e.g. the well known Rice-Ramsperger-Kassel-Markus (RRKM) theory.

During deposition of protein ions, it is desired to conserve also the folding state of the protein. Thus, concerning the effects of the kinetic energy, not only the bond cleavages should be considered, but also possible modifications in the folding. During electrospray-generation of peptide or simple protein ions, these may not be able to retain their solution phase folding in the gas phase. They refold even under these mild energetic conditions and assume their gas phase folding. However, protein ions with larger mass and complicated structure need to overcome high energy barriers to change their overall folding state. The Bowers group has reported that complex proteins become desolvated during electrospray, and shrink, but they retain their basic solution-phase structure (see, for example, Bernstein, S. L.; Wyttenbach, T. Baumketner, A. Shea, J.-E., Bitan, G.; Teplow, D. B.; Bowers, M. T. Amyloid β-Protein: Monomer Structure and Early Aggregation States of Aβ42 and Its Pro19 Alloform *J. Am. Chem. Soc.;* 2005; 127, 2075-2084). Similarly, in deposition of proteins, the tertiary structures of complex proteins may not be affected easily at the soft landing conditions. Deposited ions may undergo some deformations but the basic folding state may be retained in the deposited form.

Reports in the literature on deposition of ions (which are not separated by ion mobility) show that a careful adjustment of the kinetic energy of ions being deposited and a special preparation of the receiver surface makes it possible to deposit "intact" ions which have the same conformation as in the gas phase (Ouyang, Z.; Takats, Z.; Blake T. A.; Gologan, B.; Guymon A. J.; Wiseman J. M., Oliver J. C.; Davisson V. J.; Cooks R. G. Preparing protein microarrays by soft landing of mass-selected ions. *Science* 2003, 301, 1351-1354). The authors performed mass selection and deposition experiments with proteins like lysozyme, insulin, cytochrome c, and apomyoglobin in an electrospray/linear ion trap instrument by spraying a total of 480 μL of a solution which was $10^{-7}$-$10^{-6}$ molar in each protein, forming multiply charged ions, generating an ion flux of $10^9$ to $10^{10}$ ions per second. The reported recovery for protein amounts in 10 ng range indicates that a multi layer deposition occurs in these experiments. In the present invention, a fine control of kinetic energy of the mobility-separated ions during deposition and the special preparation of the receiver surface for the type of ions to be deposited ensure a deposition with unchanged conformation. Deposited ions can form a multi-molecular layer, in particular upon repeated deposition cycles.

The chemical and physical properties of the receiver may be such that the surface can be used "as is" for further analytical determination as described above. For mass spectrometric analysis, this can be by in situ laser desorption ionization (with or without matrix) or by extraction followed by electrospray ionization. After soft landing of proteins like lysozyme on self assembled monolayer surfaces bearing carboxyl and pyridine N-oxide functional groups, successful in-situ detection by MALDI mass spectrometry is reported. Glycerol based liquid surfaces have been found to provide a suitable soft landing medium for protein ions because they offer the possibility of resolvation upon landing, as described in the above mentioned paper (Ouyang, Z.; Takats, Z.; Blake T. A.; Gologan, B.; Guymon A. J.; Wiseman J. M., Oliver J. C.; Davisson V. J.; Cooks R. G. Preparing protein microarrays by soft landing of mass-selected ions. *Science* 2003, 301, 1351-1354). Deposition surfaces covered with a glycerol based deposition medium offer another convenience for the analytical determination of the deposited ions: Glycerol is a popular matrix for infrared MALDI if an Erbium-YAG laser is used for desorption.

Following the deposition, the receiver will be used for further analytical determination of the species separated according to their ion mobilities. Transferring the receiver into a mass spectrometer for analysis upon e.g. matrix assisted laser desorption ionization (MALDI) is one of the preferred methods. Also surface enhanced laser desorption ionization (SELDI) can be used with prepared surfaces. Electrospray mass spectrometry of the deposited ions is also an option, when the adequate receiver is used. For electrospray, a solvent has to be used to extract end spray the deposited species. Deposited ions can also be desorbed from the surface of the receiver using an ambient pressure desorption-electrospray ionization method (DESI) technique, or other ambient atmospheric ionization methods. Although mass spectrometry, in particular MALDI-MS, is a very popular method to analyze compounds deposited on adequate receivers, other analytical methods will also benefit from this deposition. The deposited species can be used for many surface analysis techniques including photoelectron spectroscopy (PES), atomic force microscopy (AFM), scanning/tunneling microscopy (STM), confocal microscopy, and surface plasmon resonance (SPR). Also biochemical analytical techniques could be applied, including various forms of immunoassays, and biosensors such as quartz crystal microbalance (QCM). Also, if desired, separated and deposited analytes may be extracted from receiver surface using liquid extraction and transferred to the secondary analytical step. This could be performed manually or automatically using a liquid handling robotic system.

Figure 2:
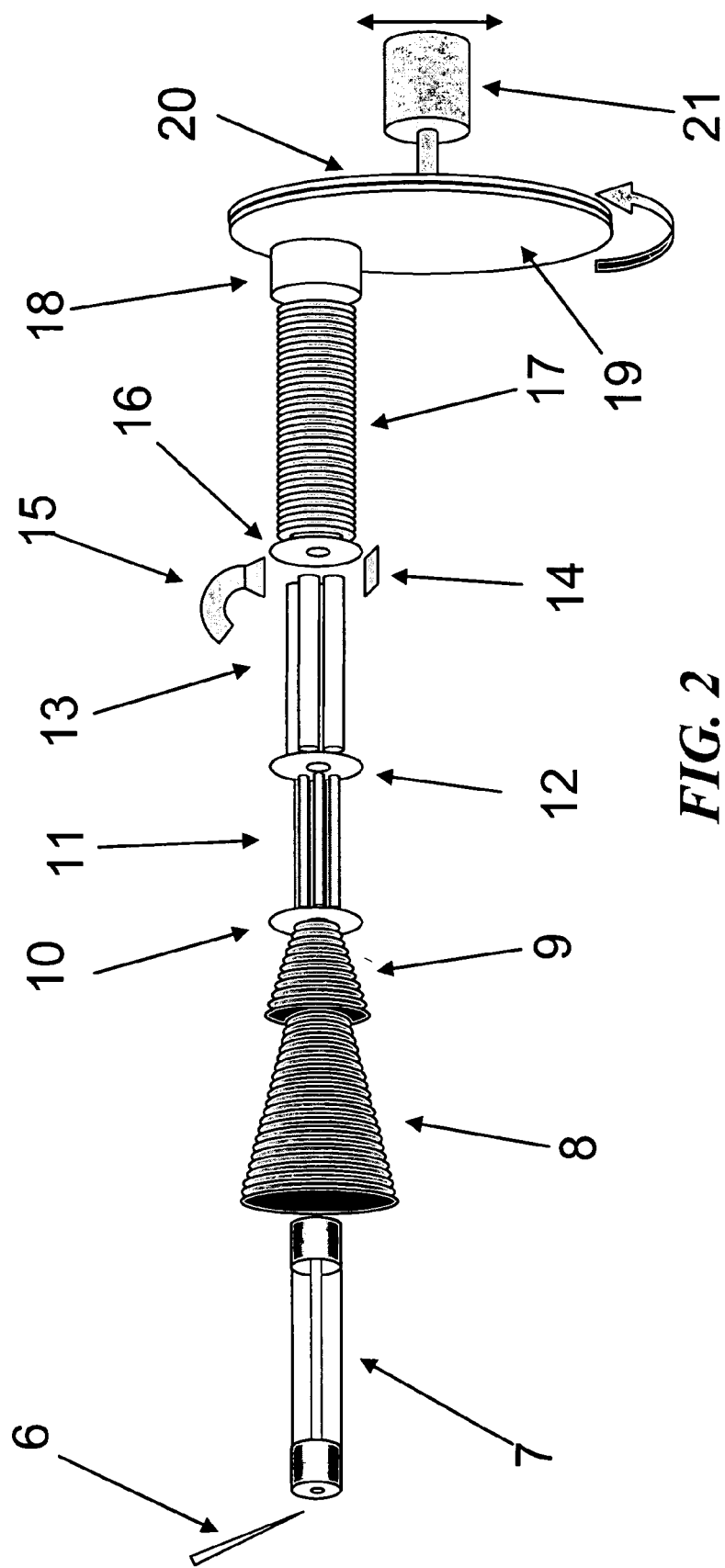
FIG. 2 shows the functional parts of a first embodiment of an ion mobility separation and deposition apparatus consisting of an ion funnel-electrospray source, an linear RF hexapole trap for ion storage, a mass selecting quadrupole, an off-axis ion detector, an ion mobility separation cell, an energy-controlling, focusing, and deflecting ion optics for deposition, and a rotating receiver for supporting the spatially separated deposition of mobility separated ions. The vacuum stages are not shown in this figure.

FIG. 2 shows the functional parts of one embodiment of a preparative ion mobility spectrometer with an electrospray ion source. The sample is introduced through the sprayer (6) and ions are generated by the electrospray processes. The ions pass a glass capillary (7) with metallized ends. Subsequently, the ions are captured by a two stage ion funnel (8, 9) system (ion funnel systems suitable for use with the inventive system are disclosed in U.S. Pat. No. 5,572,035 (Jochen Franzen) and U.S. Pat. No. 6,107,628 (Richard D. Smith and Scott A. Schaffer)) and forwarded through an apertured electrode (10) into a linear RF hexapole ion trap (11). After collecting sufficient number of analyte ions, the reflective potential at the apertured electrode (12) is reversed and the collected ions are pulsed out of the trap into a quadrupole mass filter (13). At the end of the quadrupole mass filter (13), an ion deflector (14) and an off-axis ion detector (15) is placed. Using the quadrupole mass filter (13) and the detector (15) a mass spectrum can be acquired. The mass filter is used to select ions with the mass (mass-to-charge ratio) of interest. The selected ions pass the apertured electrode (16) and are allowed to fly through the ion mobility separation cell (17) for separation the conformational isomers of the selected mass-to-charge ratio. In the ion mobility separation cell (17) the ions are in a pressure range above one millibar, and they drift under the influence of an axial electric acceleration field applied by the surrounding stacked ring electrodes of the ion mobility separation cell (17). Ions with larger geometric cross section are exposed to a larger number of collisions and drift slower, while compact ions fly faster and arrive earlier at the exit of the ion mobility separation cell (17). Following their temporal separation, the separated ions fly through an ion optical system (18). This helps to focus them and to reduce their kinetic energy for a soft landing at the surface of the receiver (19). The receiver (19) in the FIG. 2 embodiment is a round platform placed on a rotating table (20) driven by a motor (21). In addition to its rotation, the table including the motor can also make a translational motion to expose different radii of the table to deposition of mobility-selected ions.

The isomeric ions are pulsed into the quadrupole mass filter (13), selected there and transferred into the ion mobility separation cell (17). After mobility-separation the ions are deposited on spatially separated positions on the receiver plate (19). The spatial separation on the receiver (19) is provided by the fast rotation of the receiver (19). It is possible to perform repeated depositions: The ions are pulsed into the quadrupole mass filter (13), the mass selection and ion mobility separation of the isomeric ions can be repeated multiple times. The rotation frequency of the receiver (19) can be synchronized with the experiment cycle, so that during the deposition, the exact same position on the receiver can be used over and over again for the enrichment of separated isomer by repeated depositions at the same position. Thus, an accumulative deposition of mobility-separated isomeric ions can be made on the receiver (19). An increase in the accumulated amount of a mobility-selected isomeric ions permits an increase in the efficiency of the analytical determinations following the deposition process.

The off-axis detector (15) in the ion flight path between the quadrupole mass filter (13) and the ion mobility separation cell (17) shown in the FIG. 2 (and other figures) can be used to acquire mass spectrometric data in order to select ions of interest for ion mobility separation. It is practical to have the detector as an off-axis device before the ion mobility separation cell (17). However, a detector can be located at different positions. One of the possible positions of the detector can be after the ion mobility separation cell (17) at the end of flight path. The receiver can be moved away to allow the detector to detect ions. Following this event, the detector can be moved away, and the receiver can be moved in and used again.

A more convenient embodiment that uses a detector at the end of the flight path does not move the detector in or out, but instead, uses an ion deflector unit in the deposition ion optics. The deflector can move the ion beam very fast to a detector that is fixed at a side position (again off axis but at the end of the flight path). In this way, very quick ion detections can be performed.

Figure 3:
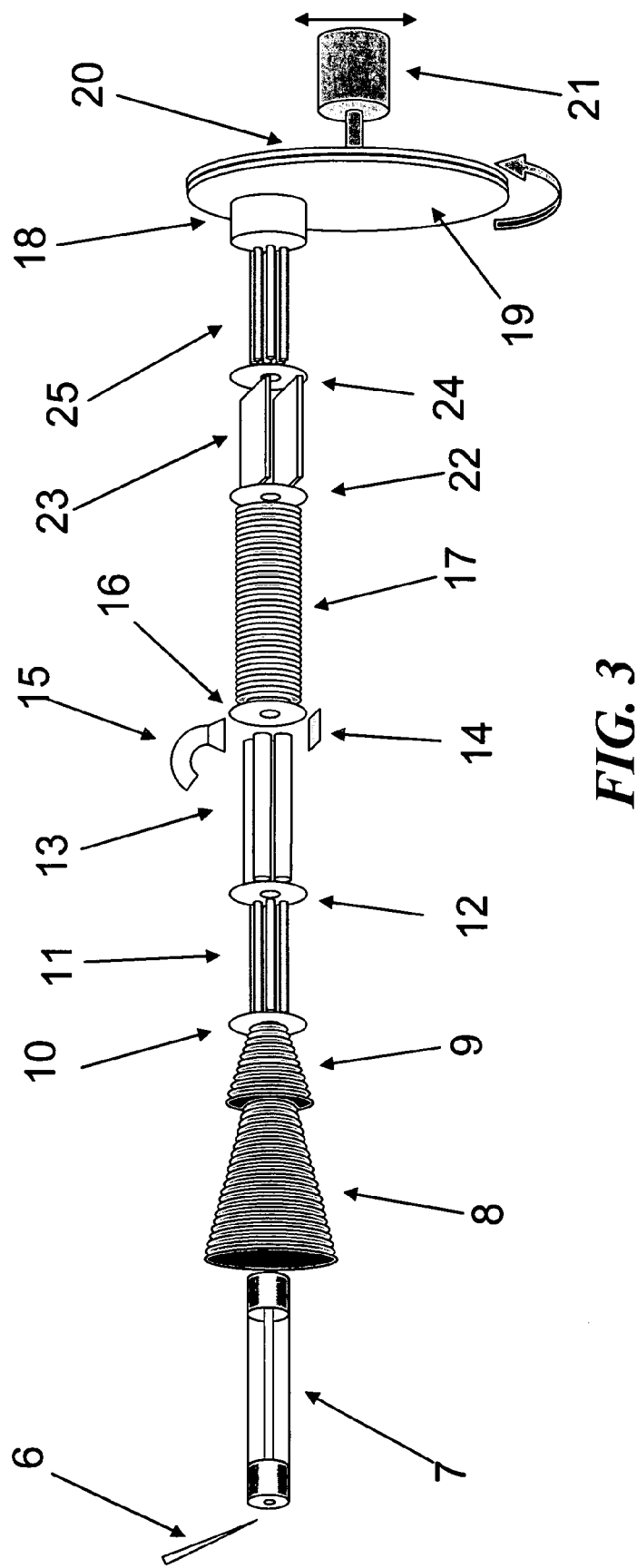
FIG. 3 shows the functional parts of a second embodiment of an ion mobility separation and deposition apparatus consisting of an ion funnel-electrospray source, an linear RF hexapole trap for ion storage, a mass selecting quadrupole, an off-axis ion detector, an ion mobility separation cell, an ion selector, another linear RF hexapole trap for ion collection, an ion optics for deposition, and a rotating receiver for supporting the spatially separated deposition of mobility separated ions. The vacuum stages are not shown in this figure.

FIG. 3 shows the functional parts of another embodiment of a preparative ion mobility spectrometer similar to the one shown in FIG. 2. However, in this embodiment, the separated ions exiting the mobility separation cell (17) enter the remainder of the apparatus through an apertured electrode (22) an ion selector (23), and later through another aperture (24) into a linear RF hexapole ion trap (25) before they are deposited. The ion selector (23) is schematically shown in FIG. 3 as a simple electrical deflector made of two electrode plates. Alternatively, it can also be made as a multi electrode deflection device. The ion selector (23) allows the selection of ions having a mobility within a predefined ion mobility window and helps eliminate all unwanted ions except the ions arriving in the mobility window of interest. The system in FIG. 3 allows repeated ion mobility separation of isomeric ions and collection of only one of the mobility-separated and selected isomers in a linear RF hexapole ion trap (25). After the collection the ions are extracted from the hexapole ion trap (25) and deposited through the special ion optics (18) onto the receiver (19). Also here, the receiver (19) is a round platform (20). Since the mobility-separated and selected ions can be collected in the hexapole ion trap before deposition, it is actually not necessary to have a fast movable receiver here. However, if the receiver (19) is mounted on the table (20) which can be rotated with the aid of a motor (21), this system offers then the options of both collecting ions of a predefined mobility range in the RF hexapole trap and depositing only them, or to do accumulative deposition of different mobility-separated ions of broad mobility ranges, without pre-collecting them in the RF hexapole trap.

Figure 4:
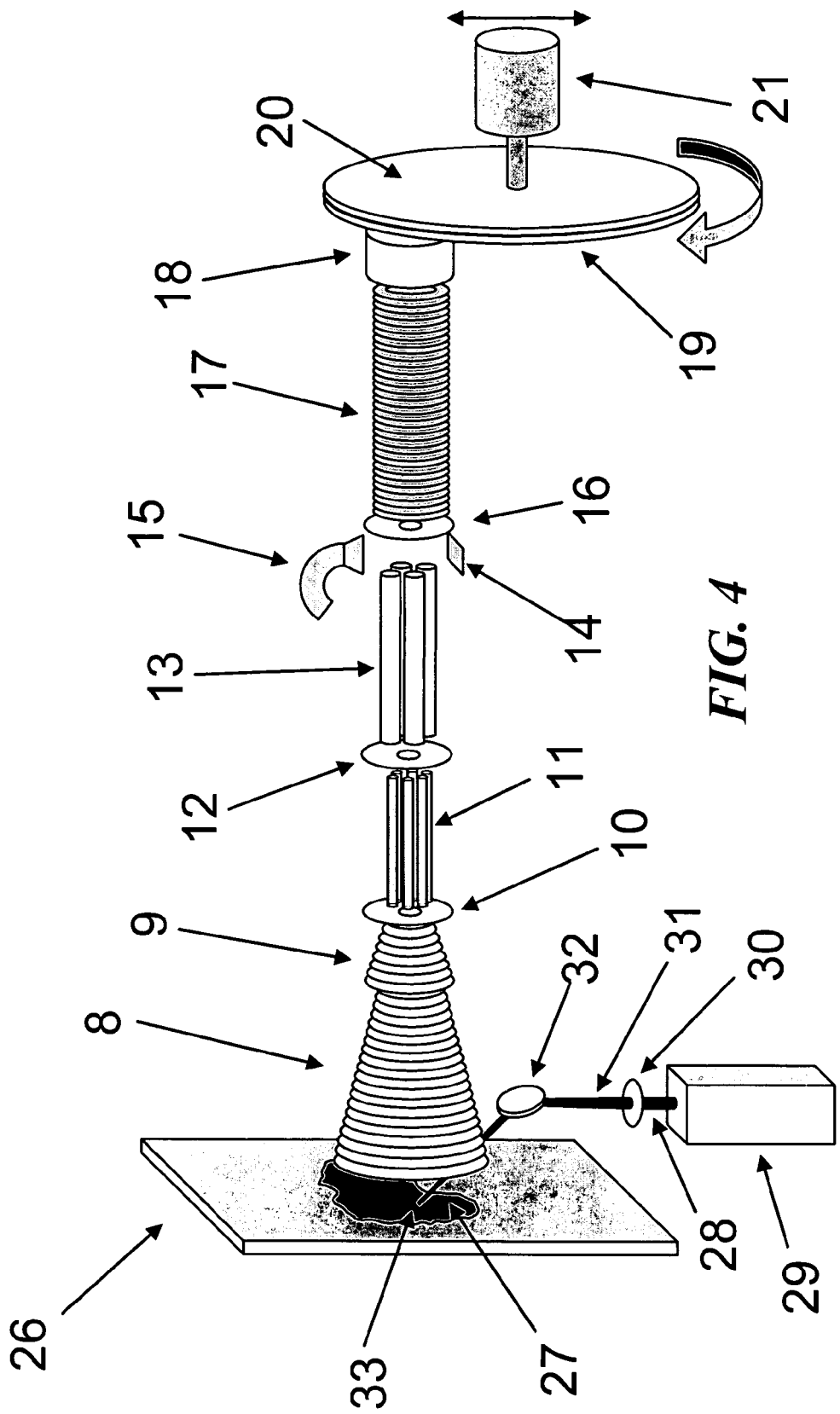
FIG. 4 shows the functional parts of a third embodiment of an ion mobility separation and deposition apparatus consisting of an ion funnel MALDI source used for MALDI-imaging of a thin tissue layer, a linear RF hexapole for ion collection, a mass selecting quadrupole, an of axis ion detector, an ion mobility separation cell, an ion optics for deposition, and a rotating receiver for supporting the spatially separated deposition of mobility separated ions. The vacuum stages are not shown in this figure.

FIG. 4 shows the functional parts of another embodiment of a preparative ion mobility spectrometer for ion mobility separation of MALDI-generated ions. In the last decade, MALDI mass spectrometry gained a new application for biological discoveries called MALDI-imaging. A tissue slice can be placed at the laser target and biological ions can be been desorbed directly from the tissue. This method allows to the equipment to raster complex tissue slices, such as animal brain slices, and obtains the corresponding mass spectra to each raster element and assigns the spectra to the corresponding points on the tissue. An image of the tissue consisting of the mass spectra gives a distribution of biomolecules of interest and allows discovering the functions as well as dysfunctions of organisms (such a system is described in U.S. Pat. No. 5,808,300 (Richard M. Caprioli)).

In this example, ions are generated from a tissue sample on a MALDI target plate (26). The tissue sample (27) can be, for example, a slice of a rat brain and be prepared with an adequate matrix (for instance 2,5-dihydroxybenzoic acid) for ionization by matrix-assisted laser desorption. The laser beam (28) is generated by the laser (29) is focused by the lens (30) and the convergent beam (31) is reflected at a mirror before hitting the spot (33) at the tissue sample (27). Generated ions fly through the ion funnels (8) and (9) and collected in the first RF hexapole (11). Ions from multiple laser shots can be collected in this hexapole (11). Subsequently, they are extracted out of the RF hexapole trap (11) by reversing the trap potential's polarity at the apertured electrode (12) and enter a quadrupole mass filter (13). The mass-selected ion type flies through the mobility separation cell (17), and the separated isomers are deposited by soft landing onto the surface of the receiver (19) on spatially separated positions. The receiver (19) in the embodiment illustrated in FIG. 4 is also a round platform placed also on a rotating table (20) driven by the motor (21). In addition to its rotation, the rotating table including the motor can also make a translational motion in order to expose different radii of the table to the deposition of the mobility-selected ions.

In the state of the art mass spectrometric MALDI imaging experiments the mass spectral data of the compound desorbed from the spot are correlated to this particular spot. The assignment of mass spectra to each desorbed spot of the tissue sample results in a map that is a relationship of geometry and chemistry. In this embodiment of the present invention, compounds laser desorbed from the spot are selected according their mass-to-charge ratio (m/z), and they undergo ion mobility separation. Mobility-separated isomeric ions are deposited on separate spots at the receiver. This correlates the positions of the laser spot with deposited positions on the receiver. This introduces a new three-way correlation: If, for example, proteins in a complex tissue sample are studied by imaging-MALDI ion mobility separation/deposition method, the location of finally deposited ions on the receiver has the complete information about the mass-to-charge ratio, the geometric cross section arising from conformational state and the location coordinates at the original tissue sample. The properties can be used in the analysis of the deposited ions and in molecular biological study of the tissue sample. Furthermore, magnified real images made of pixels consisting of mobility-separated and deposited ions can also be generated on the receiver.

As used in the device shown in FIG. 3, in the embodiment shown in FIG. 4, an ion deflector (23), an apertured electrode (24), and a linear RF hexapole trap (25) can be placed between the ion mobility separation cell (17) and deposition ion optics (18) for collection of mobility-separated ions.

Figure 5:
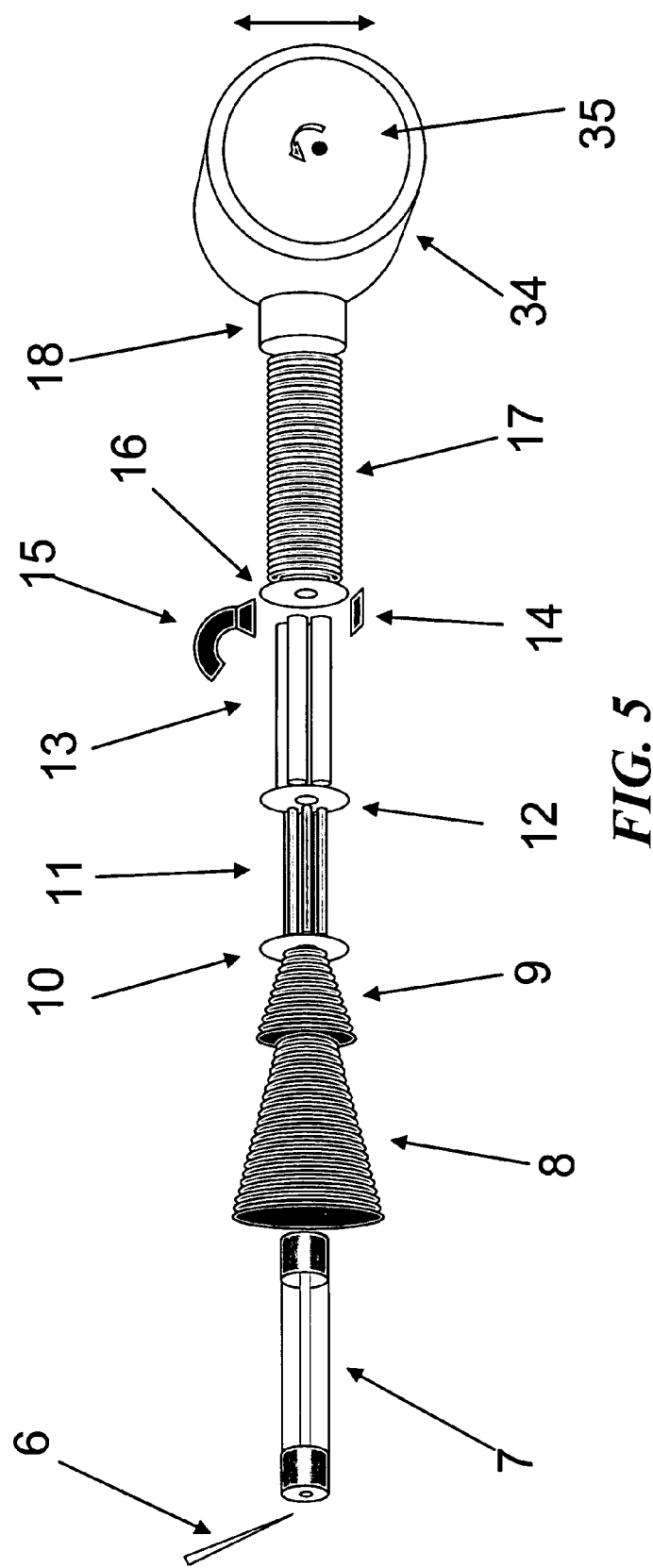
FIG. 5 shows the functional parts of a fourth embodiment of an ion mobility separation and deposition apparatus consisting of an ion funnel-electrospray source, a linear RF hexapole trap for ion storage, a quadrupole mass filter, an off axis ion detector, an ion mobility separation cell, an ion optics for deposition, and a receiver. In this case the receiver is a rotating cylindrical drum. The vacuum stages are not shown in this figure.

FIG. 5 shows the functional parts of still another embodiment of a preparative ion mobility spectrometer that ionizes the samples in an electrospray source. Similar to the embodiment in FIG. 2, in this embodiment, ions are mass selected, mobility-separated and deposited on a receiver (34). In this case, the receiver (34) is of cylindrical shape and placed on the mantle of a drum-shaped carrier (35) that rotates around an axis perpendicular to the axis of the ion mobility spectrometer. After completion of the ion mobility separation and deposition process, the receiver is removed and placed into an analysis instrument.

Implementing ion storage systems like linear RF multipole ion storage devices offer the possibility of collecting the generated ions (a) before the quadrupole mass selection to increase the ion population, (b) after the quadrupole mass selection for increasing the mass-selected ion population entering the ion mobility separation cell, or (c) after the ion mobility separation and ion selection in order to increase the mobility-selected ion population before the ion deposition.

Figure 6:
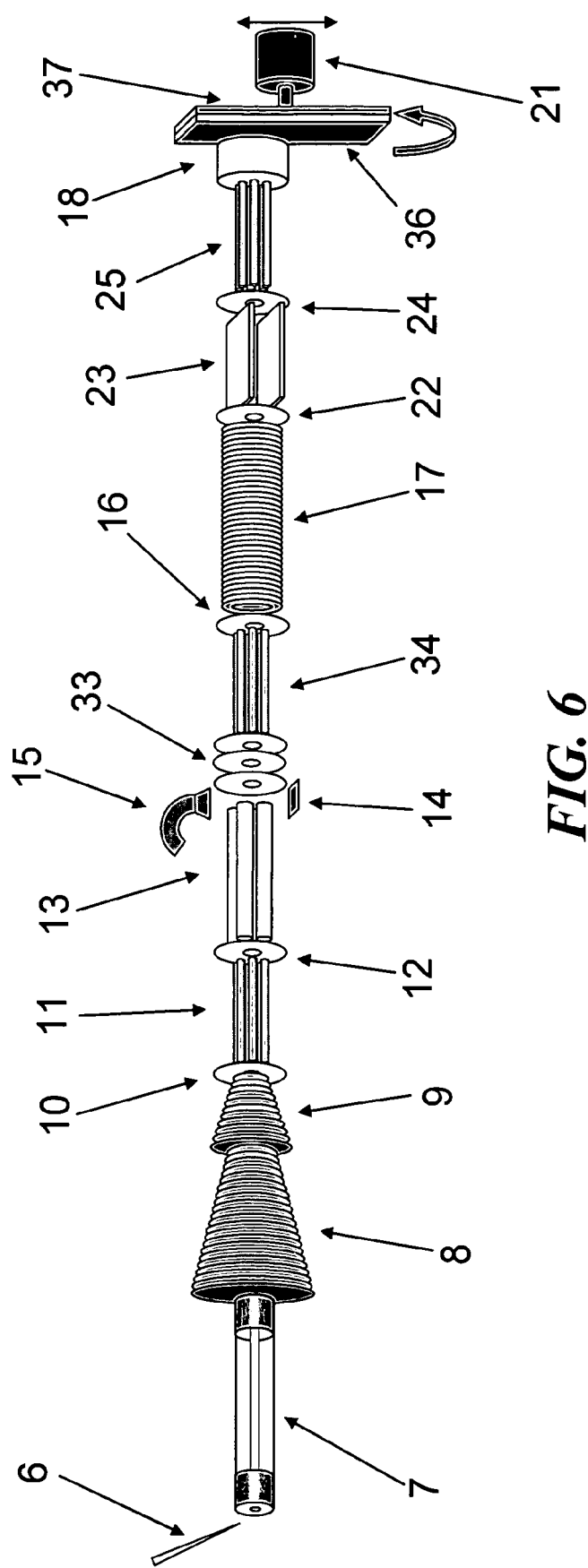
FIG. 6 shows the functional parts of a fifth embodiment of an ion mobility separation and deposition apparatus consisting of an ion funnel-electrospray source, a linear RF hexapole trap for ion accumulation, a mass selecting quadrupole, an of axis ion detector, a second RF hexapole, an ion mobility separation cell, an ion selector, a third linear RF hexapole ion trap, an energy-controlling, focusing, and deflecting ion optics for deposition, and a receiver. The vacuum stages are not shown in this figure.

FIG. 6 shows yet another embodiment of a preparative ion mobility mass spectrometer similar to the device illustrated in FIG. 3. The spectrometer shown in FIG. 6 has an additional capability of accumulating ions after the mass-to-charge selection in the quadrupole (13) before their ion mobility separation in the ion mobility separation cell (17) and deposition on the receiver (36). Once the ions are generated and passed through the quadrupole mass selector (13), the lens (33) right after the quadrupole mass selector (13) focuses the selected ions into the additional linear RF hexapole ion trap (34). Ions from repeated ion generation and selections can be collected here before they undergo ion mobility selection. This way, the number of ions of the selected mass-to-charge ratio is increased before the ion mobility separation. After the ion mobility cell, an ion selector (23) between two apertured electrodes (22) and (24) and a linear RF multipole trap (25) (in this case hexapole) trap is placed in sequence. The ion selection device (23) schematized here as a simple two-plate ion deflector, helps selecting ions of a predefined ion mobility range to collect these ions in the linear RF hexapole trap (25) before the deposition onto the receiver (36).

Having three different linear RF hexapole ion traps this device offers the possibility of collecting (a) all generated ions in the first linear RF hexapole trap (11), (b) mass selected ions in the second linear RF hexapole trap (34), and/or (c) mobility-separated and selected isomeric ions in the third linear RF hexapole trap (25) before continuing the process.

The receiver (36) in this particular case is shown to be a rectangular plate (36). It can rotate around its center of mass, as it is placed onto a rotating platform (37) driven by a motor (21). If only ions of a predefined ion mobility range desired to be deposited, a fast motion of the receiver (36), or the deposition ion beam is not necessary.

Figure 7:
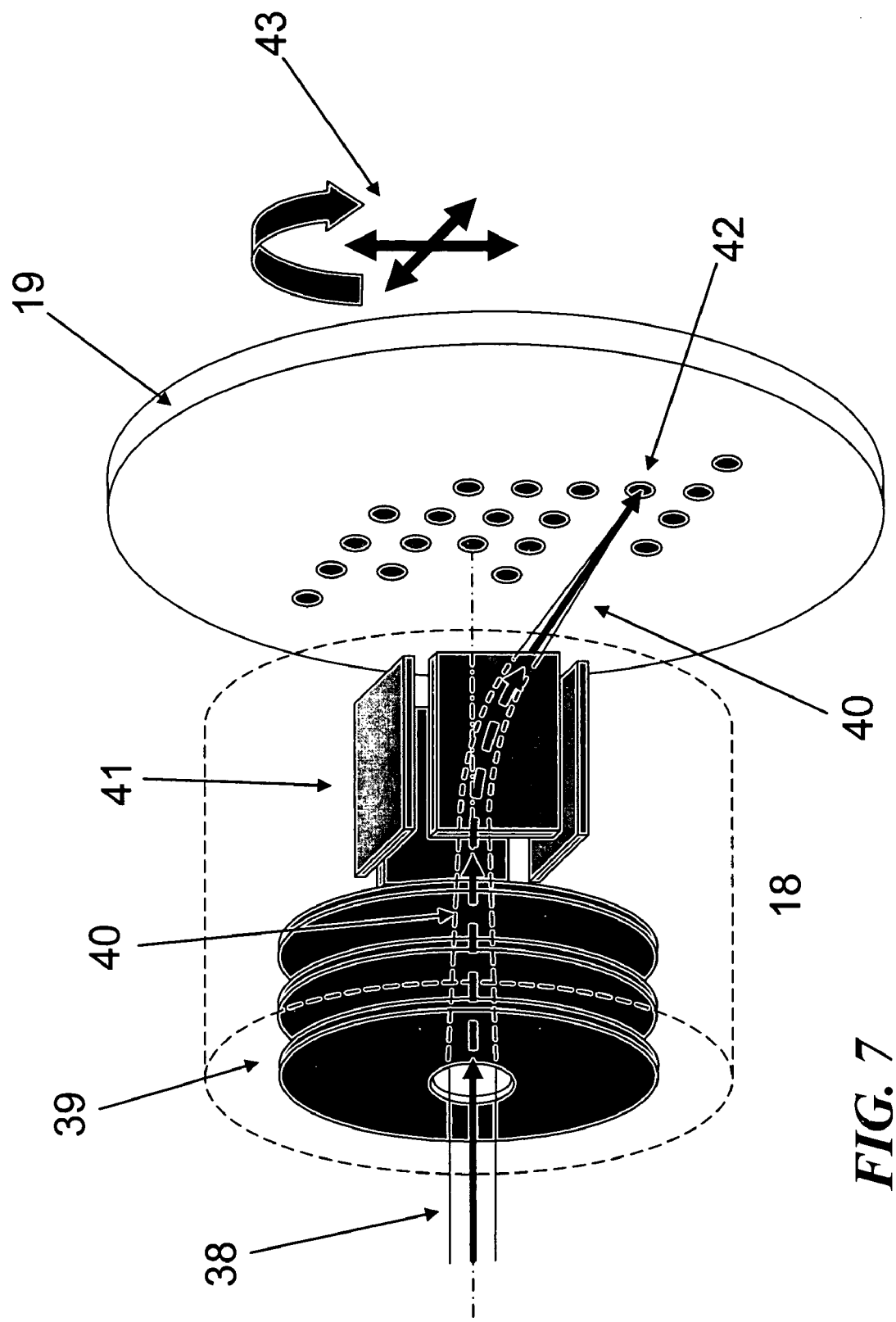
FIG. 7 shows an embodiment of an energy controlling, focusing, and deflecting ion optics unit for deposition. The unit contains an ion lens and a two-dimensional ion deflection system. Ions to be deposited arrive from separation, pass the deposition ion lens and are deflected to the separated spots on the receiver and deposited. A rotational or translational motion of the receiver can also accompany the motion of the deflected beam to increase the relative speed of switching between spots during deposition of mobility separated ions.

FIG. 7 schematically shows an example for the deflecting and energy controlling ion optics unit (18) for deposition of ions. A beam of ions to be deposited (38) comes from a mobility separation cell, passes the deposition ion lens system (39) where it is focused to become a convergent ion beam (40), goes through the deflector (41) where the ions in the beam can be deflected off the initial flight axis to one of the separated spots (42) on the receiver (19) and deposited. The receiver itself can also be moved by a rotational or translational motion (43) to support the fast spot switching of the mobility separated ions to be deposited. Electrodes that are constructed as metal-coated deposition spots on an electrically insulating background surface of specially built receivers can support the deposition process, as well as the deflection process for spatial separation. The deposition beam can be diverted to the spots of selection by changing the electrical potential of the spot. Also a receiver containing a pattern of electrodes (implemented as deposition spots each of which is connected to an electric potential) can be designed to focus, divert, and decelerate ions being deposited. If an ion deposition needs to conserve the chemical structures, it has to be a soft landing and thus the energy has to be reduced and carefully controlled while ions approach the receiver.

As the ion optics illustrated in FIG. 7 offer the option to focus the ion beam during deposition, the beam (38) can be used in a focused way for ion deposition. However, ions can be deposited also with an unfocused ion beam to form a larger spot at the receiver surface. A factor that plays a significant role in deciding whether or not to focus the ions during deposition is e.g. the analytical method to be applied for the subsequent analysis of the deposited ions.

Ion storage devices, e.g. RF hexapole ion guides, integrated to the ion mobility spectrometer can be used under elevated pressures of a collision gas as fragmentation chambers. Collision induced fragmentation of ions can be performed in any of the RF hexapole ion traps. A fragmentation of ions in such a fragmentation chamber allows the ion mobility separation of the generated fragments to be used for further structural information. The fragmentation of a mobility-separated isomeric ion before its deposition can be used to obtain additional structure-specific data.

Fragmentation by collisions (collision induced dissociation, CID) is only one of the numerous ion fragmentation methods to obtain structural information. Fragmentation in the ion mobility spectrometer of the present invention can also be achieved when ions are excited by sequential absorption of infrared photons. Infrared multiphoton dissociation (IRMPD) can also be used leading to fragment ion patterns similar to those by CID. Other methods often used in proteome research include electron capture dissociation (ECD), where the absorption of a low-energy electron by the multiply protonated molecule leads to a dissociation, or electron transfer dissociation (ETD), where an electron transfer from a negative ion to a multiply protonated molecule leads to the fragmentation of the latter. For multiply charged negative ions, electron detachment dissociation (EDD) can be used. Also metastable atom induced decomposition (MAID) is a fragmentation method for obtaining structural information.

Figure 8:
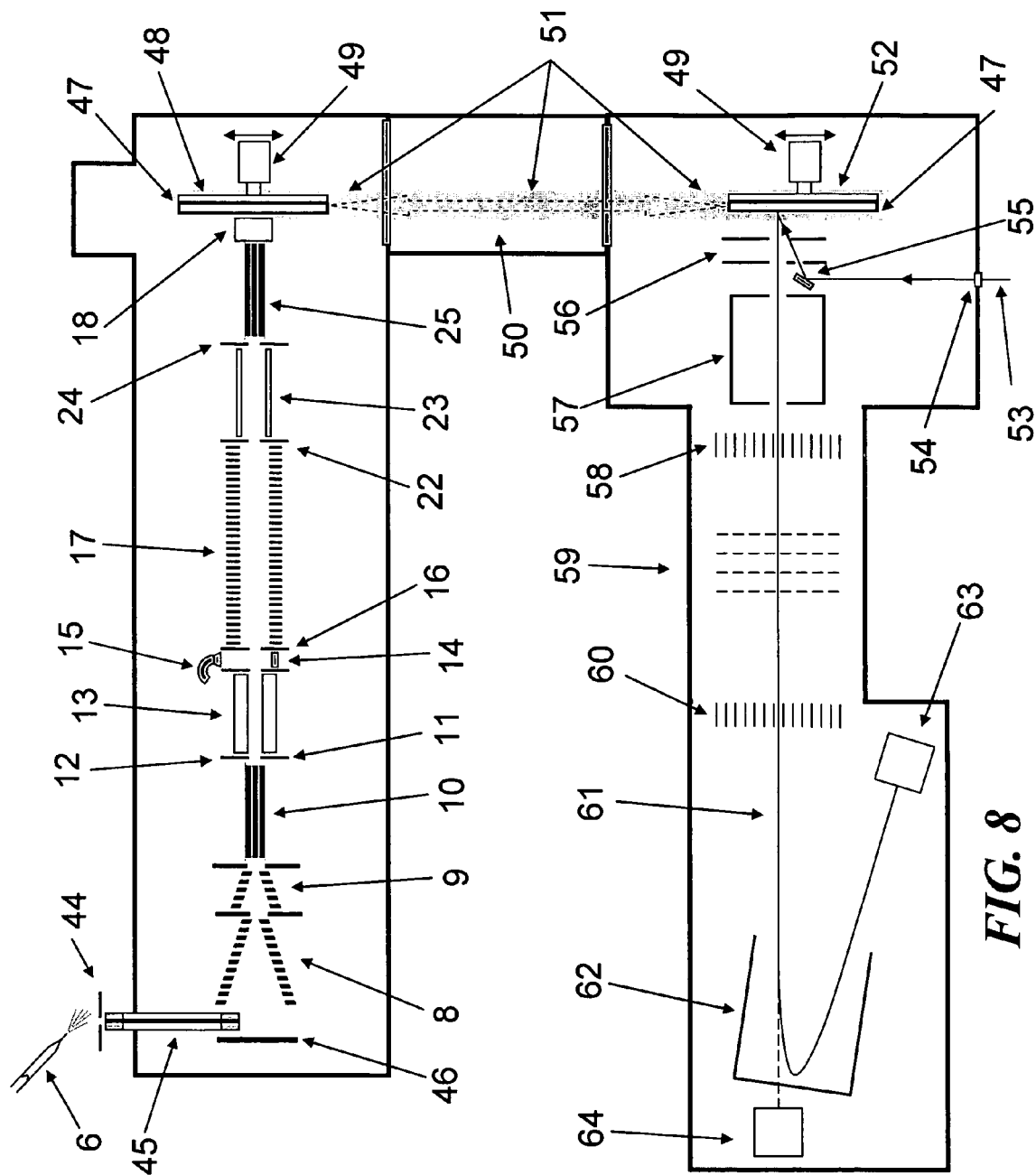
FIG. 8 shows the combination of an ion mobility separation and deposition system with a MALDI-TOF mass spectrometer. The ion mobility system ion this figure is basically the same as that illustrated in FIG. 3. However, in this specific case, the receiver is a laser target plate for MALDI mass spectrometry application. The system shown here has a transfer chamber including a vacuum lock between the ion mobility deposition part and the mass spectrometer.

The receiver of the preparative ion mobility spectrometer can be a laser target plate to be used in a MALDI time-of-flight mass spectrometer. The target plate already may contain laser desorption matrix before any deposition of mobility-separated ions. After deposition of the mobility-selected ions, this plate can be transferred in the mass spectrometric vacuum system for MALDI time-of-flight mass spectrometry. FIG. 8 schematically shows an embodiment of a complete mass analysis system where the preparative ion mobility spectrometer is just a part of the mass analysis system. The preparative ion mobility spectrometer is similar to the one described in FIG. 3. The ion source of the ion mobility separation system is an electrospray source with an angled sprayer (6) an end cap (44) and a glass capillary (45) with both ends metallized which however is orthogonal to the ion funnels (8) and (9). Ions exiting the electrospray capillary turn by a 90° angle, due to the attractive potential of the funnel (8) and the reflective potential of the repeller plate (46), fly into the ion funnels (8) and (9). Neutral droplets continue their way perpendicular to the axis of the funnels and do not enter the ion mobility spectrometer. After the funnels, ions enter the linear RF hexapole trap (13) and the ion mobility separation cell (17). They can be accumulated in the RF hexapole (25) or deposited onto the receiver (47) which is mounted on the rotating table (48) driven by a motor (49). Also here the motor can be repositioned by a linear movement for deposition of mobility-separated ions on spots at different radii.

The receiver (47) is moved through a transfer chamber (50) with a vacuum lock, by a transfer device (51) from the ion mobility spectrometer to the mass spectrometric vacuum system. The ion mobility system has a higher internal pressure than the MALDI time-of-flight mass spectrometer. The transfer of the receiver to the MALDI source of the mass spectrometer as schematized in FIG. 8 can be a simple process, if the receiver already contains the matrix for the laser desorption. Depositions on surfaces covered with glycerol based fluids can be used for infrared MALDI afterwards. Depositions that have to be performed without a matrix, require the matrix to be applied after the deposition. In this case, the transfer chamber (50) will have to contain a matrix application device, to prepare the receiver (47) for the MALDI process. The receiver plate (47) is transferred and placed in the ion source of a TOF/TOF mass spectrometer, capable of performing MS/MS fragmentation on selected ions. The carrier (52) here is also rotatable, driven by a motor, which can also positioned by a translational motion. A laser beam (53) enters the mass spectrometric vacuum system through the laser window (54), is reflected at the mirror (55) and hits the laser target at one of the spots deposited after ion mobility separation. Ions formed from this spot travel from the receiver plate through ion lenses (56) into a collision cell (57) and through the timed ion selector (58), through the second source (59) and through the metastable ion suppressor (60). The ion beam (61) then enters the gridless reflector (62) reflected and detected at the detector (63) or it is not reflected and detected in the detector (64) behind the reflector.

Figure 9:
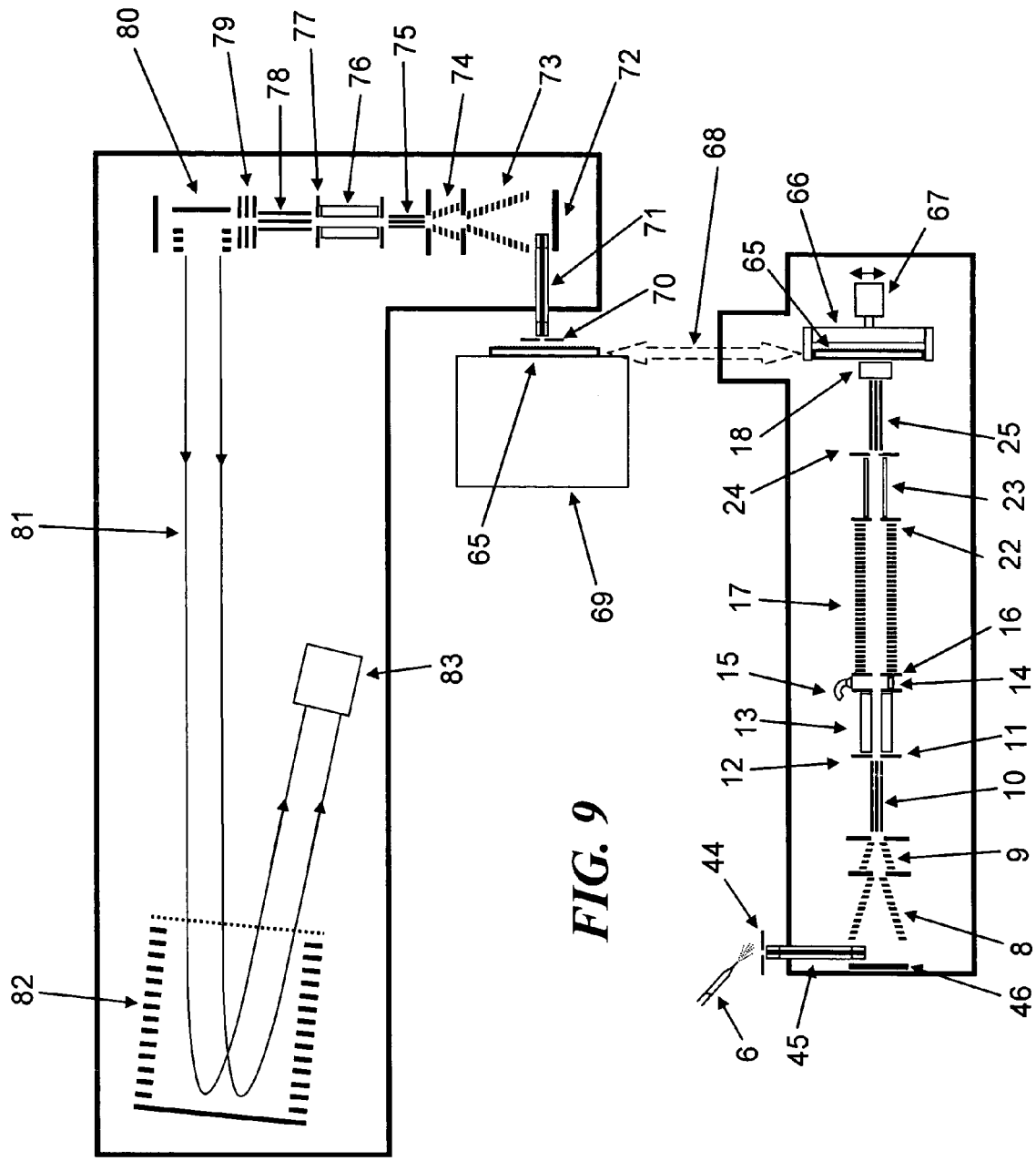
FIG. 9 shows an ion mobility separation and deposition system, basically the same as that illustrated in FIG. 3. However, in this case the receiver is a multi-nozzle nano-electrospray chip. The deposition occurs to the backside of a multi nozzle nanospray chip. After deposition, the spray chip is moved externally to the electrospray source of an orthogonal TOF mass spectrometer.

FIG. 9 shows the functional parts of an additional embodiment of a preparative ion mobility spectrometer and a mass spectrometric analysis system. The ion mobility spectrometer here is basically the same as the one described in FIG. 8, except the receiver (65) and the receiver mount (66). In this embodiment, the mobility-separated ions are deposited on the back of a multi-nozzle nanospray array plate (65). Unlike the receivers, which are used in MALDI mass spectrometry, on this multi nozzle array receiver (65) the deposition takes place on the back side of the receiver. The plate is placed in a mount (66) and its rotation is driven by the motor (67), which also can be moved translationally. After the completion of the deposition of mobility-separated ions onto the receiver (65), the receiver is removed (68) and placed in a nanospray apparatus (69). The electrospray solution enters the multi-nozzle plate from the back, dissolves the deposited species, and sprays/ionizes them. The sprayed ions enter through the end plate (70) the electrospray capillary (71) and are reflected 90° by the repeller (72) potential and the potential of the ion funnel (73). The ions pass through the two stage funnels (73) and (74) the RF hexapole (75), the quadrupole mass selector (76), the lens plate (77) and the RF hexapole trap (78), which is used as collision cell here. If collision induced dissociation is required, it is performed here. After exiting the collision cell (78) the ions pass a lens system (79) and enter the orthogonal extraction system (80) for starting their flight in the time-of-flight mass spectrometer. The extracted ion beam gets accelerated to its previous axis and follows the path (81) to the reflector (82) with grid and after reflection it is directed to the detector (83) for analysis.

What is claimed is:

1. An ion mobility spectrometer, comprising:
   an ion source that generates ions from substances,
   an ion mobility separation cell that receives ions from the ion source and separates the ions with regard to their drift time in the cell,
   an ion-selector that receives mobility-separated ions from the ion mobility separation cell and selects mobility-separated ions of one ion mobility,
   a receiver having a surface on which the selected ions are deposited, and
   means for controlling a temperature of the receiver surface during deposition.

2. The ion mobility spectrometer according to claim 1, further comprising means for causing relative motion between the receiver and the mobility-separated ions so that the mobility-selected ions are deposited on the receiver at spatially separated positions.

3. The ion mobility spectrometer according to claim 1, wherein the ion mobility separation cell comprises a mechanism that generates an RF multipole electric field that is positioned to guide the ions and prevent radial diffusion of the ions as the ions drift through the mobility separation cell.

4. The ion mobility spectrometer according to claim 1, further comprising an ion-optical device that is located between the ion mobility separation apparatus and the receiver and is constructed to focus, kinetic energy-control, and deflect the mobility-selected ions for deposition on the receiver surface.

5. The ion mobility spectrometer according to claim 1, wherein the receiver surface consists of one of a physically, chemically, biochemically, or biologically treated surface.

6. The ion mobility spectrometer according to claim 1, wherein the receiver comprises a sample holder for mass spectrometric analysis.

7. The ion mobility spectrometer according to claim 6, wherein the sample holder for mass spectrometric analysis comprises a matrix for ionization by matrix assisted laser desorption.

8. The ion mobility spectrometer according to claim 6, wherein the sample holder for mass spectrometric analysis comprises a sample holder suitable for use in an electrospray ionization unit.

9. The ion mobility spectrometer according to claim 1, wherein the receiver is a sample holder for physical, chemical, surface analytical and biochemical analysis of ions deposited thereon.

10. The ion mobility spectrometer according to claim 1, further comprising a fragmentation chamber.

11. The ion mobility spectrometer according to claim 1, further comprising an ion trap located between the ion selector and the receiver that receives and collects the mobility-selected ions.

12. A mass analysis system for analyzing ions generated from a substance, the system comprising:
    an ion mobility spectrometer that separates the ions by their mobility and has a vacuum system,
    a receiver located in the vacuum system of the ion mobility spectrometer and having a surface on which mobility-separated ions are deposited,
    a mass spectrometer having a vacuum system separate from the ion mobility spectrometer vacuum system, and
    a mechanism, operable after mobility-separated ions have been deposited on the receiver, that moves the receiver from the vacuum system of the ion mobility spectrometer into the vacuum system of the mass spectrometer so that material deposited on the receiver can be analyzed by the mass spectrometer.

13. A method for separating substances, comprising:
    (a) generating ions from substances,
    (b) separating the ions generated in step (a) by their ion mobility,
    (c) selecting from the mobility-separated ions produced in step (b) ions of one ion mobility by an ion selector, and
    (d) depositing the ions selected in step (c) on a receiver, and
    (e) temperature-controlling the receiver in step (d) for adjustment of one of a physical and chemical property of one of the receiver and a coating at the receiver surface.

14. The method according to claim 13, wherein step (c) comprises collecting selected ions in an ion trap before step (d).

15. The method according to claim 13, wherein, in step (c), ions of a second ion mobility are selected and in step (d) the selected ions of the second ion mobility are deposited on a second position on the receiver.

* * * * *